United States Patent [19]

Sunago et al.

[11] Patent Number: 4,476,512
[45] Date of Patent: Oct. 9, 1984

[54] MONITOR DEVICE FOR LASER SYSTEMS TRANSMITTING LASER LIGHT THROUGH OPTICAL FIBERS

[75] Inventors: Katsuyoshi Sunago; Shinya Takenaka, both of Osaka, Japan

[73] Assignee: Sumitomo Electric Industries, Ltd., Osaka, Japan

[21] Appl. No.: 394,248

[22] Filed: Jul. 1, 1982

[30] Foreign Application Priority Data

Jul. 2, 1981 [JP] Japan ................................ 56-97625

[51] Int. Cl.³ ............................................. H02H 5/04
[52] U.S. Cl. ................................. 361/103; 128/303.1; 219/121 LB; 219/121 LZ
[58] Field of Search ...... 219/121 LZ, 121 L, 121 LA, 219/121 LB, 121 LV, 240, 241, 510; 250/257; 128/303.1, 395, 397, 398, DIG. 22; 307/117; 340/584, 595, 596; 361/1, 103, 106

[56] References Cited

U.S. PATENT DOCUMENTS

| | | | |
|---|---|---|---|
| 3,383,491 | 5/1968 | Muncheryan | 219/121 LZ |
| 3,688,295 | 8/1972 | Tsoras et al. | 340/595 X |
| 3,942,030 | 3/1976 | Olsen et al. | 340/584 X |
| 4,311,142 | 1/1982 | Machida | 128/303.1 |

FOREIGN PATENT DOCUMENTS

| | | | |
|---|---|---|---|
| 2800123 | 7/1979 | Fed. Rep. of Germany | 250/227 |
| 2800124 | 7/1979 | Fed. Rep. of Germany | 250/227 |

*Primary Examiner*—Harry E. Moose, Jr.
*Attorney, Agent, or Firm*—Sughrue, Mion, Zinn, Macpeak, and Seas

[57] ABSTRACT

A monitor device for use in a laser system transmitting laser light through an optical fiber includes a heat-sensitive element which produces an output to monitor the laser system, the element being provided in a predetermined area of the fiber.

2 Claims, 3 Drawing Figures

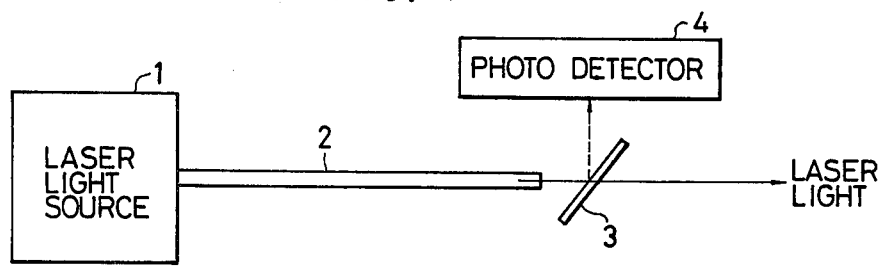
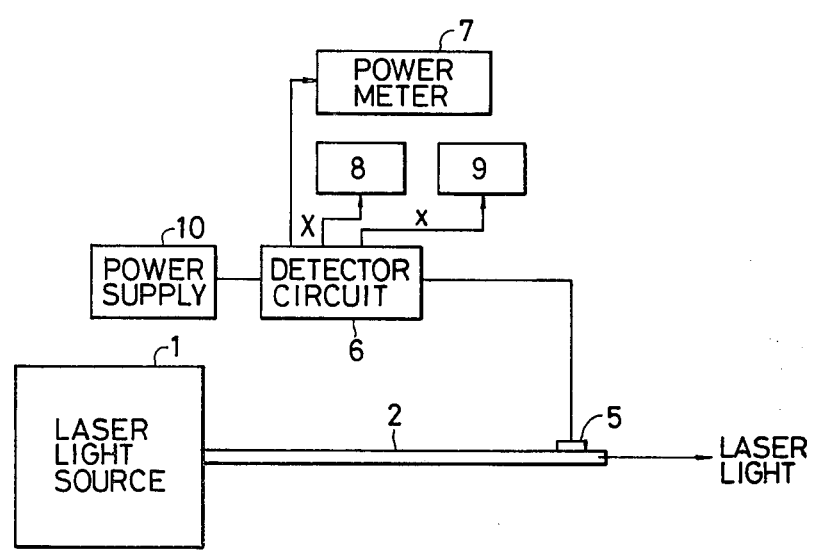

MONITOR DEVICE FOR LASER SYSTEMS TRANSMITTING LASER LIGHT THROUGH OPTICAL FIBERS

BACKGROUND OF THE INVENTION

The present invention relates to a monitor device for use in laser systems designed to transmit laser light through optical fibers.

Most laser systems, typically those used in medical applications such as the laser scalpel and the laser coagulator, produce laser light through optical fibers. These laser systems require monitor systems for monitoring the output laser power, as well as for detecting a damaged fiber or abnormal laser light source.

FIG. 1 is a schematic representation of one conventional system for monitoring the output laser power at the output end of the fibers. In the drawings, the numeral 1 indicates the laser light source, 2 is a fiber for guiding the laser light, 3 is a beam splitter such as a half mirror positioned at the output end of the fiber 2, and 4 is a heat-sensitive or light-sensitive element for receiving part of the laser beam directed through the beam splitter 3 and producing an output for monitoring the laser power (energy level).

This conventional system has the following disadvantages:

(1) Power loss results from the use of part of the output light for monitoring purposes, which is very uneconomical if the system is used for around-the-clock monitoring;

(2) Extra space is necessary at the output end of the fiber 2 for positioning the beam splitter 3 in order to branch the laser light.

SUMMARY OF THE INVENTION

The primary object of the present invention is to provide a monitor device which is free from the defects of the conventional technique; i.e., one which needs no special optical system and which involves no substantial power loss resulting from the separation of a part of the output laser light for monitoring purposes.

This object can be achieved by monitoring the laser power and other factors with a heat-sensitive element which measures the amount of heat generated by the light guide fiber. This technique is based on the finding that the light guide fiber generates a definite quantity of heat when the laser light is transmitted through the fiber. When the light from a $CO_2$ laser or a YAG (yttrium-aluminum-garnet) laser is passed through the fiber, a significant amount of heat is generated at the input or output end, or at the center of the fiber. The amount of heat generated increases with the power density of the laser light passing through the fiber. If such factors as the conditions of heat dissipation to the exterior of the fiber, the material of the fiber and the wavelength of the laser light are given, the power density is immediately determined by the density of the transmitted energy. Therefore, by knowing the temperature of a heat-sensitive element positioned at the output end of the fiber, the output laser power or the power of the laser light that reaches the output end of the fiber can be determined. Of course, the laser power at the input end or at the center of the fiber can be determined by knowing the temperatures of the respective areas, and the power of the output laser power can be calculated by correcting for the loss resulting from these areas. Reflection at end surfaces of the fiber is believed to be the primry cause of the heat generation, and while the largest amount of heat is generated at such input and output ends of the fiber, a certain amount of heat is also generated in the center. A broken fiber in the center is also a cause of substantial heat generation.

BRIEF DESCRIPTION OF THE DRAWINGS

FIG. 1 is a schematic representation of a conventional monitoring system;

FIG. 2 is a block diagram illustrating the basics of the monitoring system according to this invention.

DETAILED DESCRIPTION OF THE PREFERRED EMBODIMENTS

Figure 3:
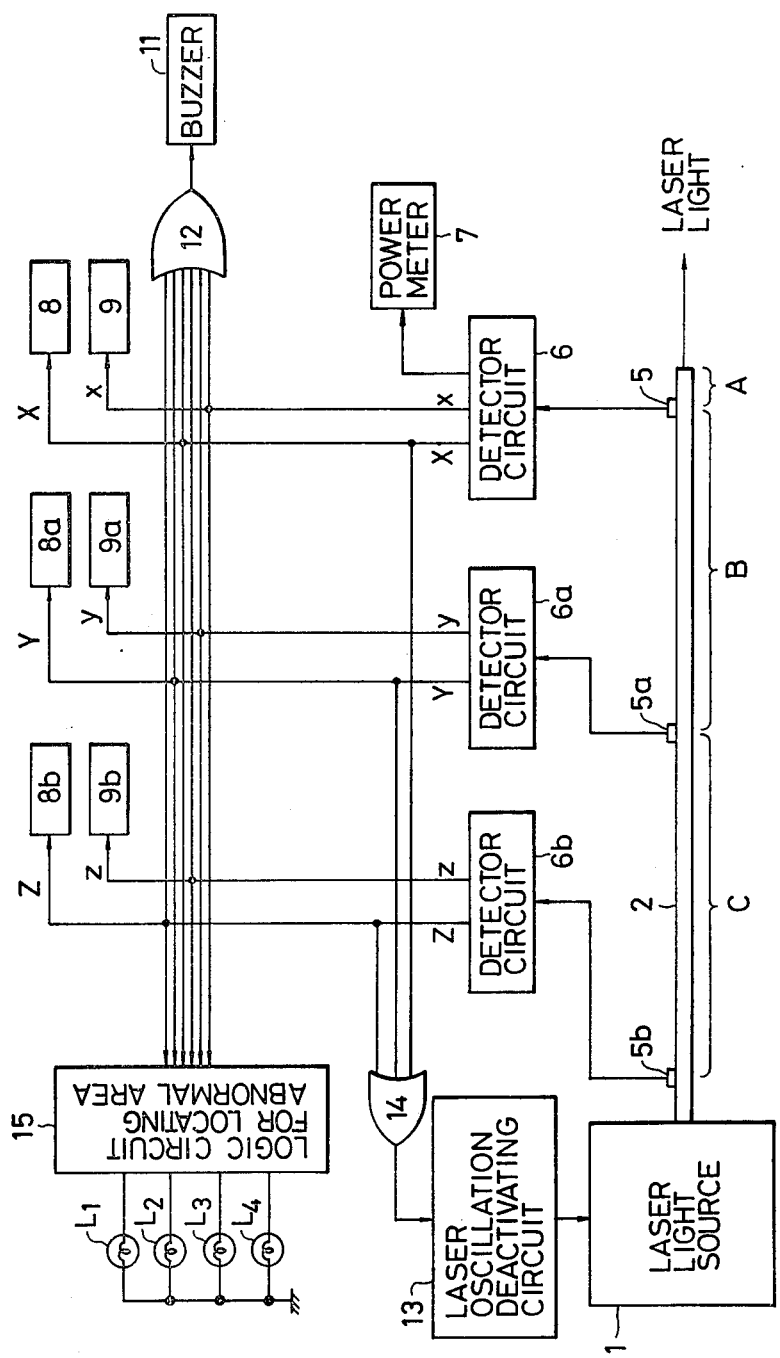
FIG. 3 is a circuit diagram of another embodiment of the invention.

FIG. 2 is a block diagram of the basic monitor device of the present invention. The circuit comprises a fiber 2 which includes a heat-sensitive element 5 provided near the output end thereof, and the output from the heat-sensitive element 5 is delivered to a detector circuit 6. The heat-sensitive element 5 is small, having a diameter of about 1-2 mm. A thermistor having a temperature durability of about 300° C. may be applied thereto. In the illustrated embodiment, the detector circuit 6 provides an analog or digital power meter 7 with a signal indicative of the magnitude of the laser power according to the output from the element 5, and at the same time, the detector compares the output of the element 5 with upper and lower limits and produces a signal X that drives an indicator 8 for indicating an abnormal increase in the laser power, and a signal x that drives an indicator 9 for indicating an abnormal decrease in the laser power. The block diagram also includes a power circuit 10. One advantage of the embodiment of FIG. 2 is that it does not separate out part of the laser light for monitoring purposes and hence no loss in the output energy occurs. Also, since no branching optical system is necessary, a small-size monitor device may serve the purpose. Signals X and x from the detector circuit 6 can be used to operate safety systems such as an alarm or a laser oscillation deactivator circuit.

FIG. 3 is a circuit diagram of another embodiment of the monitor device of the present invention, wherein heat-sensitive elements are positioned at a plurality of parts of the fiber to achieve a very precise detection of abnormalities in the laser light source 1 and fiber 2. FIG. 3 includes heat-sensitive elements 5a and 5b positioned at the center and input end, respectively, of the fiber 2; and a detector circuit 6a which receives a signal from the heat-sensitive element 5a to produce signals Y and y that indicate an abnormal increase and decrease, respectively, in laser power at the center of the fiber.

A detector circuit 6b receives a signal from the heat-sensitive element 5b to produce signals Z and z indicating an abnormal increase or decrease, respectively, in the laser power at the input end of the fiber. An alarm 11, such as a buzzer, produces an alarm when any one of the abnormal signals X, Y, Z, x, y or z is produced. An OR circuit 12 receives the X-z inputs for this purpose.

A laser oscillation deactivating circuit, such as a power breaker, discontinues laser oscillation when any of the signals X, Y and Z is produced to secure safety; and a logic circuit 15 for locating the abnormal area causes lamps $L_1$ to $L_4$ to be lit to indicate an abnormality in the laser light source, or in the respective areas A, B and C of the fiber. If all of the signals, X, Y and Z indicate an abnormal increase, or if all of the signals x, y and z indicate an abnormal decrease, the cause is detected as being in the laser light source 1. If only the signal X is produced, an irregular reflection may have occurred at a broken output end A of the fiber 2. If only the signal x is produced, a fiber may have been broken in part B, for example. FIG. 3 also includes abnormal increase indicators 8a and 8b, and abnormal decrease indicators 9a and 9b, each typically being a lamp. Indicators 8a and 9a are connected to the outputs from detector circuit 6a and indicators 8b and 9b are connected to the outputs from detector circuit 6b. In a modification of the present invention, a safety mechanism may be included that uses the output signals from the individual detector circuits to drive the alarm or a safety circuit in any desired manner. More accurate checking for the damaged part of the fiber 2 can be accomplished by increasing the number of locations where the heat-sensitive elements are provided.

What is claimed is:

1. A monitor device for a laser system transmitting laser light through an optical fiber, comprising:
   an optical fiber;
   heat-sensitive means for producing an output to monitor the laser system, said means being attached to the exterior of said fiber at a predetermined, localized area of the fiber, said area being a small fraction of the total area of said fiber; and
   an abnormality detection circuit receiving an output of said heat-sensitive element for actuating safety means, said abnormality detection circuit comprising means for detecting both an abnormal increase and an abnormal decrease in laser power, said safety means being actuated for both conditions.

2. A monitor device according to claim 1, wherein said heat-sensitive means includes a plurality of heat-sensitive elements positioned at a plurality of locations in a longitudinal direction of the fiber, said monitor device further including logic circuit means for comparing the outputs from the respective heat-sensitive elements, to determine which part of the laser system is in an abnormal state.

* * * * *